US00PP25913P3

(12) United States Plant Patent
Cain

(10) Patent No.: US PP25,913 P3
(45) Date of Patent: Sep. 22, 2015

(54) GRAPEVINE 'IFG EIGHTEEN'

(50) Latin Name: *Vitis vinifera*
Varietal Denomination: IFG Eighteen

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 99 days.

(21) Appl. No.: 13/999,132

(22) Filed: Jan. 22, 2014

(65) Prior Publication Data

US 2015/0208564 P1 Jul. 23, 2015

(51) Int. Cl.
*A01H 5/00* (2006.01)

(52) U.S. Cl.
USPC ..... Plt./205

(58) Field of Classification Search
USPC ..... Plt./205
See application file for complete search history.

*Primary Examiner* — Annette Para

(57) ABSTRACT

This invention is a new and distinct grapevine variety denominated 'IFG Eighteen'. The new grapevine is characterized by producing obtuse ovate grapes ripening in mid to late season and which have red skin color, medium firm texture and pronounced muscat flavor. The fruit stores and ships well and fruits retain their muscat flavor well during cold storage.

1 Drawing Sheet

Latin name of the genus and species claimed: *Vitis vinifera*. Variety denomination: 'IFG Eighteen'.

BACKGROUND OF THE INVENTION

The new and distinct grapevine described and claimed herein originated from a hand pollinated cross of IFG 01034-069-096, an unnamed seedless selection from the IFG breeding program and the IFG 01054-082-239 another unnamed seedless selection from the IFG breeding program hybridized in May 2004. The abortive seed traces were subsequently embryo cultured and the resulting plant was planted in the field in April 2005. The present variety of grapevine was selected as a single plant in 2006 and was first asexually propagated by hardwood cuttings in December 2006 near Delano, Kern County, Calif. The resulting propagules were planted during April 2007 near Delano, Kern County, Calif. and were found to reproduce true-to-type through at least two generations of asexual reproduction.

BRIEF SUMMARY OF THE INVENTION

The new grapevine 'IFG Eighteen' is characterized by producing medium size obtuse ovate bright red berries having soft to medium firm texture with a strong muscat flavor and which ripens in mid to late season. Berries are borne on medium size clusters which are slightly compact and may require gibberellin applications to thin clusters and size berries. Berries color moderately well and may require chemical applications to achieve good color in some climatic conditions. Berries store well and retain their muscat flavor for up to eight weeks in cold storage. To the inventor's knowledge, the known variety to which the new grapevine variety is most similar is the Flame Seedless variety (unpatented). 'IFG Eighteen' differs from the 'Flame Seedless' by ripening approximately four to five weeks later, having a strong muscat flavor as opposed to the neutral flavor of 'Flame Seedless'.

'IFG Eighteen' differs from its maternal parent by producing red, medium firm berries that have a strong muscat flavor ripening mid to late season as opposed to the more crisp textured neutral flavored white fruits of the IFG 01034-069-096 which ripen early in the season. It differs from its pollen parent, IFG 01054-082-239, by ripening later, having bright red berries with a more pronounced muscat flavor, as opposed to the early ripening reddish-black berries having a slight muscat flavor of the IFG 01054-082-239.

BRIEF DESCRIPTION OF THE FIGURE

The accompanying photographic illustration in FIG. 1 illustrates in full color 'IFG Eighteen'.

The photograph was taken outdoors with indirect lighting. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Eighteen' plants grown in the vicinity of Delano, Kern County, Calif. during 2009 and 2010, and is believed to apply to plants of the variety grown under similar conditions of soil and climate elsewhere:

VINE

General:
- *Size.*—Large.
- *Vigor.*—Vigorous.
- *Density of foliage.*—Medium.
- *Productivity.*—Productive.
- *Root stock.*—Own root.
- *Training method.*—Typically spur pruned leaving 2 bud spurs.

Trunk:
- *Trunk diameter of* 4-*year-old vines at* 30 *cm above the soil line.*—6.6 cm.
- *Shape.*—Stocky to medium.
- *Straps.*—Short — split.
- *Surface texture.*—Medium.
- *Inner bark color.*—Can be any of the following colors; Greyed orange; 166C and D.

SHOOTS

Young shoot:
- *Form of tip.*—Fully opened.
- *Distribution of anthocyanin coloration of tip.*—Piping (striped).
- *Intensity of anthocyanin coloration of tip.*—Very weak.
- *Density of prostrate hairs of tip.*—Sparse.
- *Density of erect hairs of tip.*—Absent.
- *Color.*—Can be any of the following colors; Green; 144A, and 152A and B.

Woody shoot (mature canes):
- *Shape.*—Stocky.
- *Internode length.*—Medium; About 17.0 cm.
- *Width at node.*—About 1.4 cm.
- *Cross section.*—Elliptic.
- *Surface.*—Slightly striate.
- *Main color.*—Can be any of the following colors; Greyed orange; 165A and B, and 177A.
- *Density of erect hairs of nodes.*—None.
- *Density of erect hairs on internodes.*—None.
- *Growth of axillary shoots.*—Weak to medium; Approximately 7.9 cm.

Flowering shoot:
- *Vigor during flowering.*—Strong.
- *Attitude during flowering on shoots not tied.*—Semi-drooping to Drooping.
- *Color.*—Dorsal side of internodes — Green with Red stripes.
- *Color.*—Ventral side of internodes — Green.
- *Color.*—Dorsal side of nodes — Green with Red stripes.
- *Color.*—Ventral side of nodes — Green.
- *Density of prostrate hairs of nodes.*—None.
- *Density of erect hairs on nodes.*—Sparse.
- *Density of prostrate hairs on internode.*—None.
- *Density of erect hairs on internode.*—None.
- *Anthocyanin coloration of buds.*—Absent.

Tendrils:
- *Distribution on the shoot* (*at full flowering*).—Discontinuous.
- *Length of tendril.*—Medium to long; About 21.8 cm.
- *Thickness.*—Medium.
- *Color.*—Can be any of the following colors; Green; 144A and N144A and Yellow green; 152A.
- *Form.*—Bifurcated and trifurcated.
- *Number of consecutive tendrils.*—2.

LEAVES

Young leaves:
- *Color of upper surface of first four distal unfolded leaves.*—Green with bronze spots.
- *Average intensity of anthocyanin coloration of six distal leaves prior to flowering.*—Weak to medium.
- *Density of prostrate hairs between veins* (*lower surface*) .—Absent to very sparse.
- *Density of prostrate hairs on veins* (*lower surface*).—Very sparse.
- *Density of erect hairs between veins* (*lower surface*).—Absent.
- *Density of erect hairs on veins* (*lower surface*).—Sparse.

Mature leaves:
- *Average length.*—About 16.7 cm.
- *Average width.*—About 20.1 cm.
- *Mature leaf size.*—Medium large.
- *Shape of blade.*—Wedge-shaped.
- *Number of lobes.*—5.
- *Anthocyanin coloration of main veins on upper side of blade.*—Absent to very weak.
- *Mature leaf profile.*—Undulate.
- *Blistering surface of blade upper surface.*—Very weak.
- *Leaf blade tip.*—In the plane of the leaf.
- *Undulation of margin.*—Medium.
- *Thickness.*—Medium.
- *Undulation of blade between main and lateral veins.*—Slight.
- *Shape of teeth.*—Both sides convex.
- *Length of teeth.*—Medium.
- *Ratio length/width of teeth.*—Wider than long.
- *Shape of upper lateral sinuses.*—Closed to lobes slightly overlapping.
- *Depth of upper lateral sinuses.*—Shallow to medium.
- *General shape petiole sinus.*—Half open.
- *Shape of base of upper leaf sinuses.*—V-shaped.
- *Tooth at petiole sinus.*—Absent.
- *Density of prostrate hairs between veins on lower surface of blade.*—Absent to very sparse.
- *Density of erect hairs between veins on lower surface of blade.*—Absent.
- *Density of prostrate hairs on main veins on lower surface of blade.*—None.
- *Density of erect hairs on main veins on lower surface of blade.*—Sparse.
- *Density of prostrate hairs on main veins on upper surface of blade.*—None to very sparse.
- *Density of erect hairs on main veins on upper surface of blade.*—None.
- *Autumn coloration of leaves.*—Leaves can be a single color or combination of colors, in a mottled pattern or on the edges of the leaves; Greyed orange; 163A and B, and greyed yellow; 162A and B, and 160A.

Upper surface:
- *Color.*—Can be any of the following colors; Green; 137A and B, and 139A.
- *Anthocyanin coloration of main veins.*—Absent.
- *Surface appearance.*—Glossy.
- *Blistering surface of blade.*—Very weak.

Lower surface:
*Color.*—Green; 138A.
*Anthocyanin coloration of main veins* (*lower surface*) .—Very weak.
*Glossiness.*—Medium.
*Surface texture.*—Smooth.
*Surface appearance.*—Semi-glossy.
Petiole:
*Length.*—About 15.1 cm.
*Length of petiole compared to middle vein.*—Equal to slightly shorter.
*Density of prostrate hairs on petiole.*—Very sparse.
*Density of erect hairs on petiole.*—None.
Buds:
*Bud fruitfulness.*—Basal: Mostly fruitful.
*Position of first fruitful shoot on previous season cane.*—$2^{nd}$ to $3^{rd}$ node.
*Time of bud burst.*—Midseason, about 3-20-12.

FLOWERS

General:
*Flower sex.*—Hermaphrodite.
*Length of first inflorescence.*—Short to medium; About 14.9 cm long by 9.9 cm wide.
*Position of first flowering and fruiting node.*—$3^{th}$ to $4^{th}$ (current season growth).
*Number of inflorescence per flowering shoot.*—1.1 to 2.
*Time of bloom.*—Midseason as compared with similar varieties in the growing area of Delano, Calif.
*Date of full bloom.*—May 14, 2012.

FRUIT

General:
*Ripening period.*—Medium late; Approximately Sep. 1, 2011.
*Use.*—Fresh market.
*Keeping quality.*—Good.
*Resistance to.*—Insects: Average; typical of *Vitis vinifera* species. Diseases: Average; typical of *Vitis vinifera* species.
*Refractometer test.*—Soluble solids: About 20.4 Brix.
*Brix/acid.*—About 40.8.
*Titratable acidity.*—About 0.48.
*Juice pH.*—About 3.87.
Cluster:
*Mature cluster length* (*peduncle excluded*).—About 25.9 cm.
*Mature cluster width.*—About 16.5 cm.
*Mature cluster weight.*—About 978 g.
*Bunch density.*—Medium.
*Number of berries.*—About 205.
*Form.*—Conical.
Peduncle:
*Lignification of peduncle.*—Strong.
*Length of peduncle.*—Short; Approximately 4.6 cm.
Berry:
*Uniformity of size.*—Uniform.
*Single berry weight.*—About 5.3 g natural; to about 8.0 g when treated with gibberellic acid.
*Shape.*—Obtuse ovate.
*Seeds.*—Absent, may occasionally have a small seed trace.
*Cross section.*—Circular.
*Berry dimensions.*—Longitudinal axis: About 2.1 cm. horizontal axis: About 1.9 cm.
*Berry firmness.*—Soft to medium firm.
*Particular flavor.*—Muscat.
*Bloom* (*cuticular wax*).—Medium.
*Berry separation from pedicel.*—Difficult.
*Skin color* (*without bloom*).—Red-Purple 59B.
Skin:
*Thickness.*—Medium thick.
*Texture.*—Medium tough.
*Reticulation.*—Absent.
*Tenacity.*—Tenacious to flesh.

What is claimed:

1. A new and distinct variety of grapevine as herein illustrated and described.

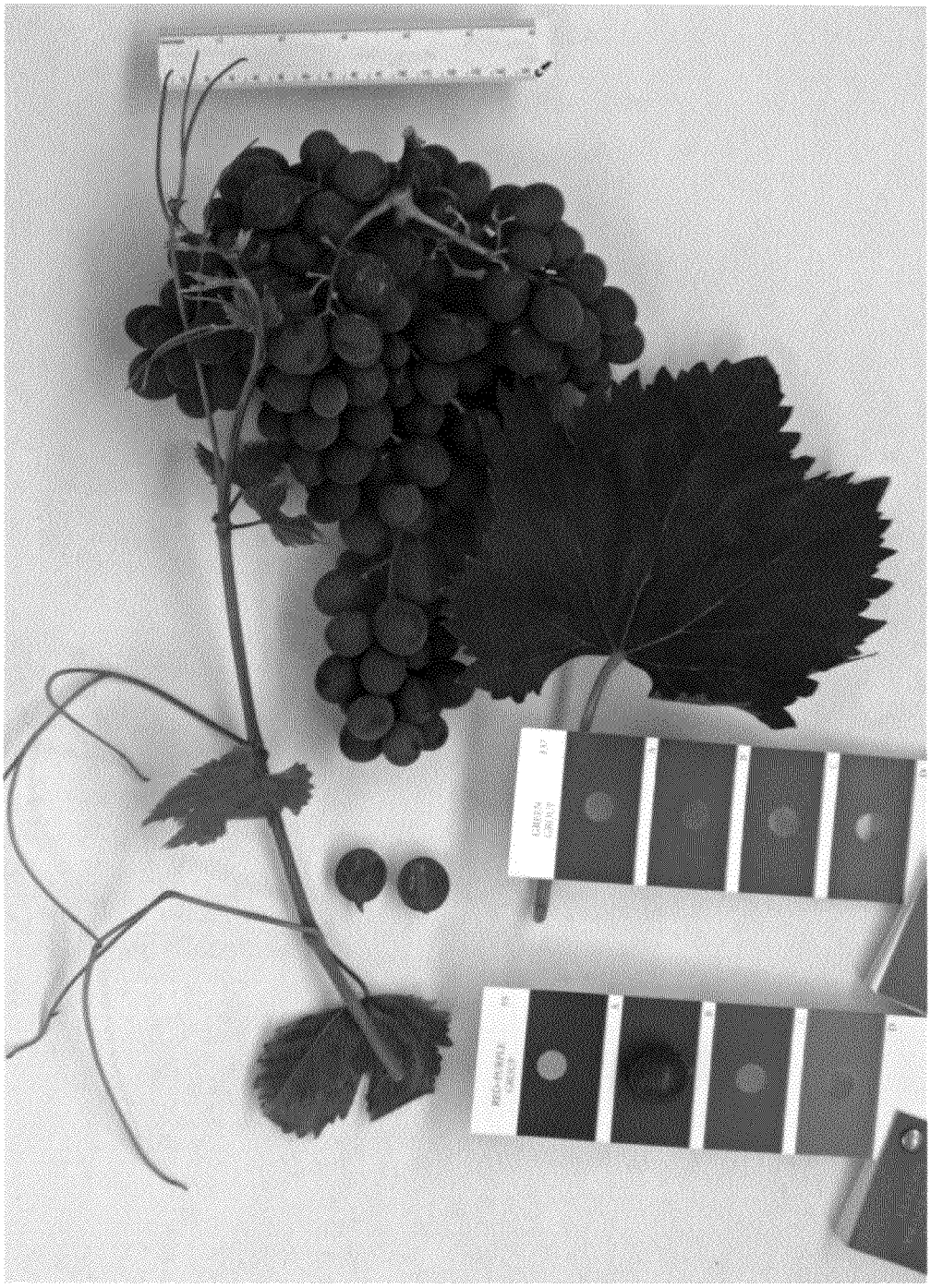

* * * * *